pattern isextendedoradjustedunder 35
U.S.C. 154(b) by 401 days.

(12) United States Patent (10) Patent No.: US 8,507,677 B2
Nagano et al. (45) Date of Patent: Aug. 13, 2013

(54) FLUORESCENT PROBE

(75) Inventors: Tetsuo Nagano, Tokyo (JP); Hirotatsu Kojima, Tokyo (JP); Kazuki Kiyose, Tokyo (JP)

(73) Assignee: The University of Tokyo, Tokyo (JP)

( * ) Notice: Subject to any disclaimer, the term of this patent is extended or adjusted under 35 U.S.C. 154(b) by 401 days.

(21) Appl. No.: 12/526,677

(22) PCT Filed: Feb. 15, 2008

(86) PCT No.: PCT/JP2008/052505

§ 371 (c)(1),
(2), (4) Date: Jul. 23, 2010

(87) PCT Pub. No.: WO2008/099914

PCT Pub. Date: Aug. 21, 2008

(65) Prior Publication Data

US 2010/0285515 A1 Nov. 11, 2010

(30) Foreign Application Priority Data

Feb. 16, 2007 (JP) ................................. 2007-035768

(51) Int. Cl.
*C07D 403/00* (2006.01)
*C07D 209/02* (2006.01)

(52) U.S. Cl.
USPC .......................................... 544/359; 548/455

(58) Field of Classification Search
None
See application file for complete search history.

(56) References Cited

U.S. PATENT DOCUMENTS

| 3,623,881 | A | 11/1971 | Fumia et al. |
| 3,695,888 | A | 10/1972 | Hiller et al. |
| 3,753,721 | A | 8/1973 | Millikan et al. |
| 3,796,573 | A | 3/1974 | Jones |
| 5,578,425 | A | 11/1996 | Dickerson et al. |
| 2007/0298507 | A1 | 12/2007 | Nagano et al. |

FOREIGN PATENT DOCUMENTS

| JP | 49-21658 | 6/1974 |
| JP | 49-46930 | 12/1974 |
| JP | 51-5780 | 2/1976 |
| JP | 62-164595 | 7/1987 |
| JP | 09-34078 | 2/1997 |
| JP | 11-149154 | 6/1999 |
| JP | 2000-35647 | 2/2000 |
| JP | 2003-501540 | 1/2003 |
| WO | 00/75237 | 12/2000 |
| WO | 2005/080331 | 9/2005 |

OTHER PUBLICATIONS

Lippard SJ. "The Art of Chemistry". Nature. 2002; 416:587.*
Dorwald FZ. "Side Reactions in Organic Synthesis: A Guide to Successful Design". Wiley VCH Verlag GmbH & Co. KGaA. 2005; p. 1-15.*

English Version of International Preliminary Report on Patentability of Chapter I dated Aug. 27, 2009.
Reichardt, C et al., Syntheses with Substituted Malondialdehydes. VI. "Preparation and Properties of γ-Arylazopentamethinecyanine Dyes", Chemische Berichte, 1970, vol. 103, No. 4, p. 1072-1087.
Gray, R. et al., "Hydrolytic Breakdown of Meso-diphenylamine Substituted Heptamethine Dye IR140 and Isomerism of the Merocyanine Breakdown Product", Dyes and Pigments, 1998, vol. 38, No. 1-3, p. 97-105.
Reichardt, C et al., Syntheses with aliphatic dialdehydes. 31. "Synthesis and Reactions of 2-(Dialkylamino) Malonaldehydes", Liebigs Annalender Chemie, 1982, No. 3, p. 530-535.
Santos, P.F. et al., "Efficiency of Singlet Oxygen of Aminosquarylium Cyanines", Journal of Photochemistry and Photobiology, A: Chemistry, 2004, vol. 163, No. 1-2, p. 267-269.
English and Japanese versions of the International Search Report for International Application No. PCT/JP2008/052505.
Japanese Office Action issued with respect to counterpart Japanese Application No. 2008-558145, dated Mar. 5, 2013, with English translation.
Yu, A. et al., "Solvatochromism and Solvation Dynamics of Structurally Related Cyanine Dyes", *J. Phys. Chem. A* vol. 106, No. 41, p. 9407-9419, 2002.
Casay, G.A. et al., "Fiber Optic Probe Applications Using Near-Infrared Compounds: Determination of NaOH", *Spectroscopy Letters* vol. 28, No. 3, p. 301-326, 1995.

* cited by examiner

*Primary Examiner* — Leslie A. Royds Draper
(74) *Attorney, Agent, or Firm* — Greenblum & Bernstein, P.L.C.

(57) ABSTRACT

A compound represented by the following general formula (I):

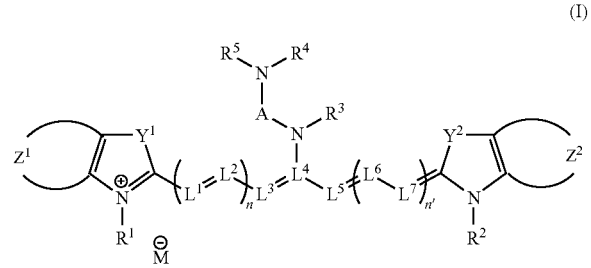

[wherein $R^1$ and $R^2$ represent a $C_{1-6}$ alkyl group; $R^3$, $R^4$ and $R^5$ represent hydrogen atom, a $C_{1-6}$ alkyl group, or an aryl group; $Y^1$ and $Y^2$ represent —O—, —S—, —Se—, —CH=CH—, —C($R^6$)($R^7$)—, or —N($R^8$)— (wherein $R^6$, $R^7$ and $R^8$ represent hydrogen atom or a $C_{1-6}$ alkyl group); A represents a $C_{1-3}$ alkylene group; n and n' represent 0, 1 or 2; $Z^1$ and $Z^2$ represent a nonmetallic atom group required to form a benzo-condensed ring or a naphtho-condensed ring; $L^1$ to $L^7$ represent a methine group; and $M^-$ represents a counter ion in a number required for neutralizing electrical charge], which is useful as a fluorescent probe of which optical characteristics change depending on pH change.

25 Claims, 5 Drawing Sheets

FLUORESCENT PROBE

TECHNICAL FIELD

The present invention relates to a fluorescent probe. More specifically, the present invention relates to a fluorescent probe which detects pH change to emit fluorescence of the near infrared region.

BACKGROUND ART

Cyanine dyes are widely used in various fields, and they are also used in the field of fluorescence imaging for studying physiological functions as fluorescence labels of biological molecules. In particular, tricarbocyanine type dyes have a maximum absorption wavelength and maximum fluorescence wavelength in the near infrared region of around 650 to 950 nm, of which lights are relatively less absorbed by biological molecules, and thus they have an advantage that they allow use of lights of a wavelength which can penetrate into deep parts of biological tissues. In addition, biological substances scarcely emit autofluorescence of the near infrared region. More specifically, the characteristics of tricarbocyanine type dyes are suitable for in vivo imaging. In addition to cyanine type dyes for directly labeling biological molecules with fluorescence, tricarbocyanine dyes which specifically react with biological molecules to change fluorescence intensity thereof have recently been developed. One of them is a near infrared fluorescent probe for calcium ions (Ozmen, B., et al., Tetrahedron Lett., 41, pp. 9185-9188, 2000), and another is a near infrared fluorescent probe for nitrogen monoxide (NO) (WO2005/080331). These fluorescent probes give only fluorescence intensity changes, but do not show changes of excitation wavelength and fluorescence wavelength, before and after a specific reaction with a biological molecule.

It is known that intracellular pH is maintained at about 6.8 to 7.4 in cytoplasm, or maintained to be acidic, i.e., about 4.5 to 6.0, in lumens of organelles such as Golgi apparatuses, small granule vesicles, coated vesicles, endosomes, and lysosomes, and that such pH changes in association with various cell responses. Such change of intracellular pH controls various cell functions, and there are various reports especially relating to physiological roles thereof in apoptosis, endocytosis, homeostasis, ion transport, and the like (Rich, I. N., et al., J. Cell Physiol., 177 (1) 109, 1998; Meisenholder G. W., et al., J. Biol. Chem., 271, 16260, 1996). Therefore, measurement of intracellular pH is important for understanding control mechanisms of intracellular reactions.

In order to measure intracellular pH, compounds which are protonated or deprotonated depending on intracellular pH, and emit fluorescence in response to the change (pH fluorescent probe) have conventionally been used. As pH fluorescent probes having the fluorescein structure as a mother nucleus, for example, BCECF (2',7'-bis(carboxyethyl)-4 or 5-carboxyfluorescein) and derivatives thereof, CFDA (carboxyfluorescein diacetate) and derivatives thereof, SNARF-1 (seminaphthorhodafluor) and derivatives thereof ("Handbook of Fluorescent Probes and Research Chemicals", 10th Edition by Richard P. Haugland, chapter 20, "pH indicators", which is a catalogue of Molecular Probe, for all the compounds) and the like have been put into practical use. As pH probes having the cyanine structure as a mother nucleus, the compounds described in International Patent Publication WO00/75237 and CypHer (GE Healthcare Bioscience) are available.

However, BCECF and CFDA, which are pH fluorescent probes having the fluorescein structure, have an excitation wavelength not longer than 550 nm, which results in low permeability for biological tissues, and therefore they have problems in that they cannot achieve observation of deep parts of tissues, and they are readily influenced by autofluorescence of biological substances (fluorescence emitted by NADH, flavins and the like) at measurement. Further, CypHer and the pH fluorescent probes described in International Patent Publication WO00/75237 have the cyanine structure, and they emit fluorescence when the nitrogen atom of the nitrogen-containing hetero aromatic ring bonded to the polymethine chain of the cyanine structure is protonated. These fluorescent probes enable measurement with an excitation light of a long wavelength not shorter than 640 nm, and fluorescence intensity thereof increases along with the decrease of pH in the neutral region or lower pH region. Therefore, they have an advantage that they are hardly influenced by autofluorescence of biological substances. However, application of fluorescent probes to cells involves many factors which affect the measurement. For example, concentration of a fluorescent probe introduced into cells may vary depending on type of the cells, fluorescence intensity may vary depending on thickness of cell membrane even in a measurement region, a fluorescent probe may localize at a highly hydrophobic portion such as membranes, and the like.

As a method for reducing measurement errors induced by these factors to realize accurate quantitative analysis, the ratio method has been developed and used (Kawanishi Y., et al, Angew. Chem. Int. Ed., 39(19), 3438, 2000). This method comprises the step of measuring fluorescence intensities at two different wavelengths in a fluorescence spectrum or an excitation spectrum to detect a ratio thereof. In this method, influence of concentration of the fluorescent probe itself or intensity of excitation light can be neglected, and measurement errors can be eliminated, which may be caused by localization of the fluorescent probe itself, change of concentration thereof, discoloration thereof, or the like, when the measurement is performed at one wavelength.

For example, SNARF-1, which is a pH fluorescent probe having the fluorescein structure, has a property that the peak of fluorescence wavelength shifts to the longer wavelength side due to deprotonation when pH shifts to the alkaline side, and when the compound is excited around 500 nm, fluorescence intensity around 580 nm decreases along with the increase of pH, whilst fluorescence intensity around 640 nm increases with the increase of pH. Therefore, if this compound is excited at an appropriate wavelength around 500 nm, and ratio of fluorescence intensities at appropriate two wavelengths around 580 to 640 nm, pH can be accurately measured regardless of probe concentration, intensity of light source, size of cells, and the like. However, there has not been known any fluorescent probe which enables imaging of intracellular pH change by the ratio method using an excitation light of the near infrared region around 650 to 950 nm, which has superior permeability for biological tissues, and thus it has been desired to develop a fluorescent probe for measuring fluorescence of the near infrared region around 650 to 950 nm by the ratio method, which fluorescence is less influenced by autofluorescence of biological substances and has superior permeability for biological tissues, in order to accurately perform fluorescence imaging of pH change.

DISCLOSURE OF THE INVENTION

Object to be Achieved by the Invention

An object of the present invention is to provide a fluorescent probe which specifically and highly sensitively detects pH change to emit fluorescence. More specifically, the object of the present invention is to provide a fluorescent compound which can be excited with a near infrared light of around 650 to 950 nm, having superior permeability into biological tissues, and has a marked wavelength shift in the peak of the excitation spectrum upon pH change. Another object of the present invention is to provide a compound usable as a fluorescent probe for measuring a change of pH according to the ratio method by measuring near infrared fluorescence emitted when the compound is irradiated with excitation lights of two wavelengths around 650 to 950 nm. Another object of the present invention is to provide a pH fluorescent probe comprising a compound having the aforementioned characteristics and a method for measuring pH using such a pH fluorescent probe.

Means for Achieving the Object

The inventors of the present invention conducted various researches in order to achieve the objects mentioned above, and as a result, found that a compound represented by the following general formula (I) absorbed an excitation light of the near infrared region around 650 to 950 nm to emit strong fluorescence, and showed a marked wavelength shift in the peak of excitation spectrum according to pH change, and pH change was highly accurately measurable by the ratio method using the compound. They also found that, by appropriately choosing the substituent bound to the pH sensitive amino group of the compound represented by the following general formula (I), compounds having various pKa values were successfully provided, and the compounds were usable as compounds that enabled measurement of pH change around each pKa by the ratio method. The present invention was accomplished on the basis of these findings.

The present invention thus provides a compound represented by the following general formula (I);

[Formula 1]

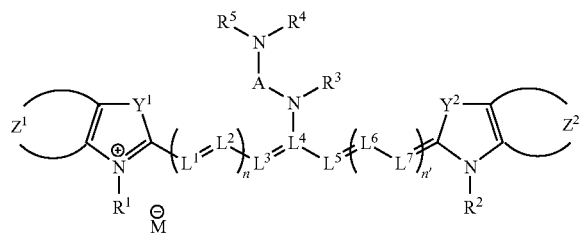

(I)

[wherein $R^1$ and $R^2$ independently represent a $C_{1-6}$ alkyl group which may have a substituent; $R^3$, $R^4$ and $R^5$ independently represent hydrogen atom, a $C_{1-6}$ alkyl group which may have a substituent, or an aryl group which may have a substituent, or $R^3$ and $R^4$ bind together to represent a $C_{1-3}$ alkylene group, or $R^3$ and $R^5$ bind together to represent a $C_{1-3}$ alkylene group, provided that $R^3$ is not hydrogen atom, and $R^3$, $R^4$, or $R^5$ is not 2-pyridylmethyl group, 2-pyridylethyl group, 2-methyl-6-pyridylmethyl group, or 2-methyl-6-pyridylethyl group; $Y^1$ and $Y^2$ independently represent —O—, —S—, —Se—, —CH=CH—, —C($R^6$)($R^7$)—, or —N($R^8$)— (wherein $R^6$, $R^7$ and $R^8$ independently represent hydrogen atom or a $C_{1-6}$ alkyl group which may have a substituent); A represents a $C_{1-3}$ alkylene group which may have a substituent; n and n' independently represent 0, 1 or 2; $Z^1$ and $Z^2$ independently represent a nonmetallic atom group required to form a benzo-condensed ring which may have a substituent or a naphtho-condensed ring which may have a substituent; $L^1$, $L^2$, $L^3$, $L^4$, $L^5$, $L^6$ and $L^7$ independently represent a substituted or unsubstituted methine group, provided that when n or n' is 2, each two of $L^1$ and $L^2$, or each two of $L^6$ and $L^7$ may be the same or different; and n represents a counter ion in a number required for neutralizing electrical charge]. This compound is useful as a pH-responsive fluorescent probe.

As a preferred embodiment of the aforementioned invention, there is provided a compound represented by the following general formula (IA);

[Formula 2]

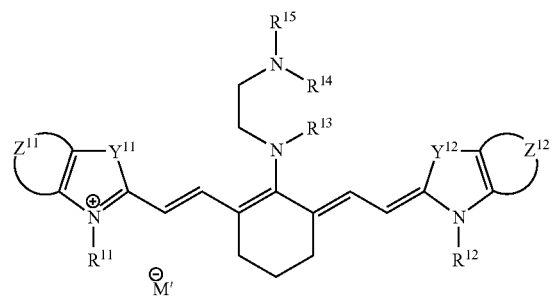

(IA)

[wherein $R^{11}$ and $R^{12}$ independently represent a $C_{1-6}$ alkyl group which may have a substituent; $R^{13}$, $R^{14}$ and $R^{15}$ independently represent hydrogen atom, a $C_{1-6}$ alkyl group which may have a substituent, or an aryl group which may have a substituent, or $R^{13}$ and $R^{14}$ bind together to represent ethylene group, provided that $R^{13}$ is not hydrogen atom, and $R^{13}$, $R^{14}$ or $R^{15}$ is not 2-pyridylmethyl group, 2-pyridylethyl group, 2-methyl-6-pyridylmethyl group, or 2-methyl-6-pyridylethyl group; $Y^{11}$ and $Y^{12}$ independently represent —O—, —S—, —Se—, —CH=CH—, —C($R^{16}$)($R^{17}$)—, or —N($R^{18}$)— (wherein $R^{16}$, $R^{17}$ and $R^{18}$ independently represent hydrogen atom or a $C_{1-6}$ alkyl group which may have a substituent); $Z^{11}$ and $Z^{12}$ independently represent a nonmetallic atom group required to form a benzo-condensed ring which may have a substituent or a naphtho-condensed ring which may have a substituent; and $M'^-$ represents a counter ion in a number required for neutralizing electrical charge].

From another aspect, the present invention provides a pH fluorescent probe, which contains a compound represented by the aforementioned general formula (I), preferably a compound represented by the aforementioned general formula (IA).

The present invention also provides a method of using a compound represented by the aforementioned general formula (I), preferably a compound represented by the aforementioned general formula (IA), as a pH fluorescent probe; use of a compound represented by the aforementioned general formula (I), preferably a compound represented by the aforementioned general formula (IA), for manufacture of a pH fluorescent probe; and a method for measuring pH change of a test object, which comprises the following steps: (a) the step of contacting a compound represented by the aforementioned general formula (I), preferably a compound represented by the aforementioned general formula (IA), with the test object, and (b) the step of measuring fluorescence intensity of the compound represented by the aforementioned general formula (I), preferably the compound represented by the aforementioned general formula (IA), after contacting in the aforementioned step (a).

Effect of the Invention

The compounds of the present invention represented by the aforementioned general formula (I) have a property that they show marked change in the fluorescent characteristic, upon protonation of a nitrogen atom that is not directly bonding to a methine chain such as $L^1$ in a substituent bonded to the methine chain, which change is induced according to pH change of, for example, an aqueous solution as a test object. Further, the compounds of the present invention represented by the aforementioned general formula (I) emit strong fluorescence upon excitation with a light of the near infrared region, and accordingly, they enable measurement of pH change in deep parts of tissues in living bodies when they are used as a fluorescent probe. Further, by suitably choosing the substituents of $R^3$, $R^4$, and $R^5$, fluorescent probes having various pKa values can be designed and provided.

BEST MODE FOR CARRYING OUT THE INVENTION

Figure 1:
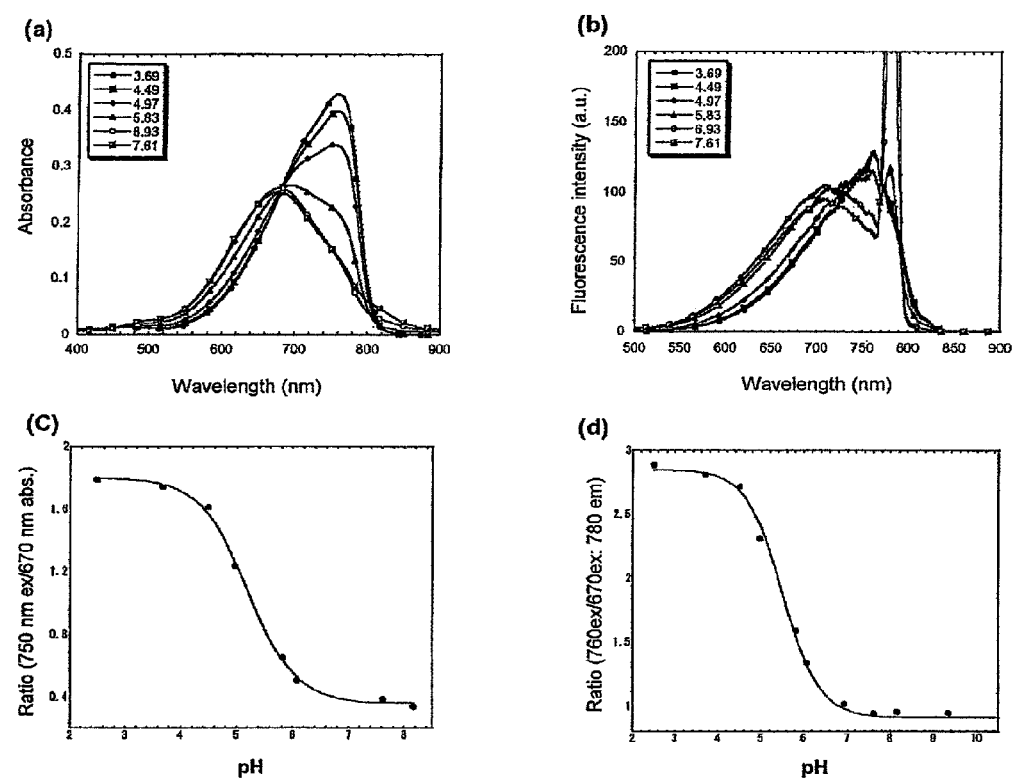
FIG. 1 shows the optical characteristics of Compound 1 at various pH values. In the drawings, (a) shows the absorption spectrum, (b) shows the excitation spectrum at a fluorescence wavelength of 780 nm, (c) shows ratio of absorption at 750 nm to absorption at 670 nm, and (d) shows ratio of fluorescence intensity at 780 nm observed with excitation at 760 nm to fluorescence intensity at 780 nm observed with excitation at 670 nm. All the measurements were performed in a 100 mM sodium phosphate buffered solution containing 10% DMSO as an auxiliary solvent.

In this specification, the alkyl group may be a linear, branched, or cyclic alkyl group, or a combination thereof, unless otherwise specifically mentioned. When the expression "which may have a substituent" is used for a certain functional group, type, number and substitution position of the substituent are not particularly limited. For example, the functional group may have an alkyl group, an alkoxy group, an aryl group, a halogen atom (it may be any of fluorine atom, chlorine atom, bromine atom, and iodine atom), hydroxy group, amino group, carboxy group or an ester thereof, sulfo group or an ester thereof, or the like as the substituent. In this specification, the aryl group may be any of a monocyclic or polycyclic aryl group, and a monocyclic or polycyclic heteroaryl group, and preferably a monocyclic or polycyclic aryl group, more preferably phenyl group, can be used.

In the general formula (I), $R^1$ and $R^2$ independently represent a $C_{1-6}$ alkyl group which may have a substituent. Examples of the alkyl group include, for example, methyl group, ethyl group, n-propyl group, isopropyl group, n-butyl group, isobutyl group, sec-butyl group, tert-butyl group, n-pentyl group, isopentyl group, neopentyl group, tert-pentyl group, 1-methylbutyl group, 2-methylbutyl group, 1-ethylpropyl group, n-hexyl group, 1-methylpentyl group, 2-methylpentyl group, 3-methylpentyl group, 4-methylpentyl group, 1,2-dimethylbutyl group, 2,3-dimethylbutyl group, 1,3-dimethylbutyl group, 1-ethylbutyl group, 2-ethylbutyl group, and the like. As the alkyl group represented by $R^1$ or $R^2$, a linear alkyl group is preferred.

Examples of the substituent which can exist on the $C_{1-6}$ alkyl group represented by $R^1$ or $R^2$ include, for example, an alkoxy group, an aryl group, a halogen atom (it may be any of fluorine atom, chlorine atom, bromine atom and iodine atom), hydroxy group, amino group, carboxy group or an ester thereof, sulfo group or an ester thereof, phospho group or an ester thereof, and the like. Among these, carboxy group, sulfo group and the like are preferred, and they can provide an effect of markedly increasing water-solubility of the compounds of the present invention. Specific example of the alkyl group which has a substituent include, for example, hydroxymethyl group, 1-hydroxyethyl group, 2-hydroxyethyl group, 2-hydroxypropyl group, 3-hydroxypropyl group, 4-hydroxybutyl group, carboxymethyl group, sulfomethyl group, 2-sulfoethyl group, 3-sulfopropyl group, 4-sulfobutyl group, and the like. Both $R^1$ and $R^2$ may be unsubstituted $C_{1-6}$ alkyl groups, or one of these $C_{1-6}$ alkyl groups may have a substituent. $R^1$ and $R^2$ preferably represent a linear $C_{1-6}$ alkyl group, or a $C_{1-6}$ alkyl group substituted with sulfo group, particularly preferably methyl group. The above explanations for $R^1$ and $R^2$ are similarly applied to $R^{11}$ and $R^{12}$ in the general formula (IA).

In the general formula (I), $R^3$, $R^4$, and $R^5$ independently represent hydrogen atom, a $C_{1-6}$ alkyl group which may have a substituent, or an aryl group which may have a substituent, or $R^3$ and $R^4$ bind together to represent a $C_{1-3}$ alkylene group, or $R^3$ and $R^5$ bind together to represent a $C_{1-3}$ alkylene group. However, $R^3$ is not hydrogen atom, and $R^3$, $R^4$ or $R^5$ is not 2-pyridylmethyl group, 2-pyridylethyl group, 2-methyl-6-pyridylmethyl group, or 2-methyl-6-pyridylethyl group. Examples of the substituent which can exist on the $C_{1-6}$ alkyl group which may have a substituent include, for example, an alkoxy group, an aryl group, a halogen atom (it may be any of fluorine atom, chlorine atom, bromine atom and an iodine atom), hydroxy group, amino group, carboxy group or an ester thereof, sulfo group or an ester thereof, and the like. Examples of the aryl group moiety of the aryl group which may have a substituent include a monocyclic or polycyclic aryl group and a monocyclic or polycyclic heteroaryl group. $R^3$ and $R^4$, or $R^3$ and $R^5$ may bind together to form a $C_{1-3}$ alkylene group, and this alkylene group may have a substituent such as an alkoxy group, an aryl group, a halogen atom (it may be any of fluorine atom, chlorine atom, bromine atom, and iodine atom), hydroxy group, amino group, carboxy group or an ester thereof, and sulfo group or an ester thereof. Among these, a combination that all of $R^3$, $R^4$, and $R^5$ are methyl groups, a combination that $R^3$ is methyl group, and Wand $R^5$ are ethyl groups, or a combination that $R^3$ and $R^4$ bind together to form ethylene group, and $R^5$ is methyl group, phenyl group, or benzyl group is preferred. The above explanations for $R^3$, $R^4$, and $R^5$ are similarly applied to $R^{13}$, $R^{14}$, and $R^{15}$ in the general formula (IA).

In the general formula (I), $R^1$ to $R^5$ may be independently a group which can be buried in a cell membrane. In such a case, the compounds of the present invention represented by general formula (I) can be used as a membrane localizing type fluorescent probe to measure pH change only around cell membranes. Linear or branched $C_{7-18}$ alkyl groups are used as the membrane-embedded group. Phospholipids, such as phosphatidylethanolamines, phosphatidylcholines, phosphatidylserines, phosphatidylinositols, phosphatidylglycerols, cardiolipins, sphingomyelins, ceramide phosphorylethanolamines, ceramide phosphorylglycerols, ceramide phosphorylglycerol phosphates, 1,2-dimyristoyl-1,2-deoxy-phosphatidylcholines, plasmalogens and phosphatidic acids, can also be used. In these phospholipids, the structure of the fatty acid chain is not restricted. Practically, saturated or unsaturated fatty acids (with 1 or 2 unsaturated bonds) composed of 12 to 20 carbon atoms can be used. As the membrane-embedded group, the $C_{1-6}$ alkyl group represented by $R^1$ to $R^5$ in the general formula (I) to which linear or branched $C_{7-18}$ alkyl groups or phospholipids are connected via the substituent which can exist on the $C_{1-6}$ alkyl group and the like are preferred. The above explanations about $R^1$ to $R^5$ are similarly applied to $R^{11}$ to $R^{15}$ in the general formula (IA).

$Y^1$ and $Y^2$ independently represent —O—, —S—, —Se—, —CH=CH—, —C($R^6$)($R^7$)—, or —N($R^8$)—, and $R^6$, $R^7$, and $R^8$ independently represent hydrogen atom or a $C_{1-6}$ alkyl group which may have a substituent. $Y^1$ and $Y^2$ are preferably —C($R^6$)($R^7$)—, and $R^6$ and $R^7$ are preferably methyl groups. A represents a $C_{1-3}$ alkylene group which may have a substituent, and it is more preferably unsubstituted ethylene group. The above explanations about $Y^1$ and $Y^2$, and $R^6$, $R^7$, and $R^8$ are similarly applied to $Y^{11}$ and $Y^{12}$, and $R^{16}$, $R^{17}$, and $R^{18}$ in the general formula (IA).

In the general formula (I), $Z^1$ and $Z^2$ independently represent a nonmetallic atom group required to form a benzo-condensed ring which may have a substituent or a naphtho-condensed ring which may have a substituent. More specifically, for example, $Z^1$ and $Z^2$ each form any of the following benzo-condensed ring and naphtho-condensed rings. The benzo-condensed ring and the naphtho-condensed ring may have a substituent such as an alkoxy group, an aryl group, a halogen atom (it may be any of fluorine atom, chlorine atom, bromine atom, and iodine atom), hydroxy group, amino group, carboxy group or an ester thereof, and sulfo group or an ester thereof. The above explanations for $Z^1$ and $Z^2$ are also similarly applied to $Z^{11}$ and $Z^{12}$ in the general formula (IA).

[Formula 3]

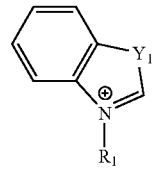

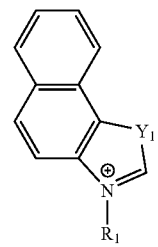

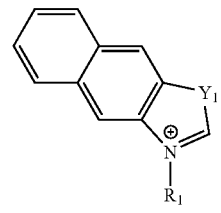

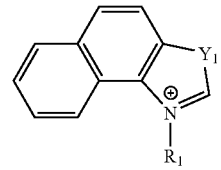

The compounds of the present invention represented by the aforementioned general formula (I) preferably show a maximum absorption wavelength in the region of 400 to 1300 nm, more preferably 650 to 950 nm, still more preferably 650 to 800 nm. Those skilled in the art would understand that as n or n' in the compounds of the present invention represented by the aforementioned general formula (I) increases, the excitation wavelength and fluorescence wavelength thereof become longer, and similarly, as n or n' decreases, the excitation wavelength and fluorescence wavelength become shorter. In the aforementioned general formula (I) of the present invention, it is preferred that the sum of n and n' is 2, and it is particularly preferred that both n and n' are 1.

$L^1$, $L^2$, $L^3$, $L^4$, $L^5$, $L^6$ and $L^7$ independently represent a substituted or unsubstituted methine group, and they may be the same or different. Further, when n is 2, two each of $L^1$ and $L^2$ may be the same or different, and when n' is 2, two each of $L^6$ and $L^7$ may be the same or different. Substituents of the methine groups represented by $L^1$, $L^2$, $L^3$, $L^4$, $L^5$, $L^6$ and $L^7$ may bind to each other to form a ring containing three contiguous methine groups, and this ring may form a condensed ring with a ring containing other methine groups. As the partial structure constituted by $L^1$, $L^2$, $L^3$, $L^4$, $L^5$, $L^6$ and $L^7$, the structures mentioned below are particularly preferred.

[Formula 4]

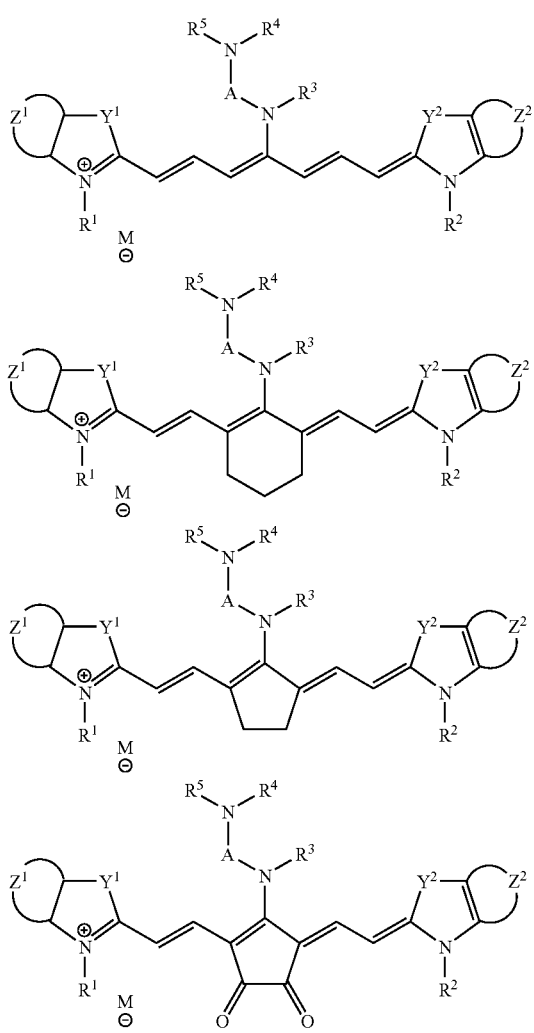

M⁻ and M'⁻ represent a counter ion in a number required for neutralizing electrical charge. Examples of the counter ion include, for example, metal ions such as sodium ion, potassium ion and magnesium ion, quaternary ammoniums, halogen ions such as iodine ion, ions of amino acids such as glycine. For example, when carboxy group, sulfo group, or the like exists on the $C_{1-6}$ alkyl group represented by $R^1$ or $R^2$ in the general formula (I), or one or more of $R^3$, $R^4$, $R^5$, $R^6$, $R^7$, $R^8$, $Z^1$, and $Z^2$ in the general formula (I) contain carboxy group, sulfo group, phospho group or the like, two or more counter ions may be needed as M. Further, when one carboxy group or sulfo group exists in the $C_{1-6}$ alkyl group represented by one of $R^1$ and $R^2$ in the general formula (I), the positive charge of the quaternary nitrogen atom to which $R^1$ binds and the anion of carboxy group or sulfo group may sometimes form an intramolecular zwitterion, and therefore the counter ion required for neutralization of electrical charge may be unnecessary.

The compounds of the present invention represented by the aforementioned general formula (I) may have one or more asymmetric carbons. Therefore, any of arbitrary optical isomers in an optically pure form, arbitrary mixtures of optical isomers, racemates, diastereoisomers in a pure form, mixtures of diastereoisomers, and the like based on one or more asymmetric carbon atoms fall within the scope of the present invention. The compounds of the present invention may exist as a hydrate or solvate, and these substances of course also fall within the scope of the present invention.

The compound of the aforementioned general formula (IA) is particularly preferably the compound wherein $R^{11}$ and $R^{12}$ are methyl group and 4-sulfobutyl group, and $Z^{11}$ and $Z^{12}$ form an unsubstituted benzo-condensed ring.

More specifically, the following compounds can be mentioned as particularly preferred compounds. However, the compounds of the present invention are not limited to these.

[Formula 5]

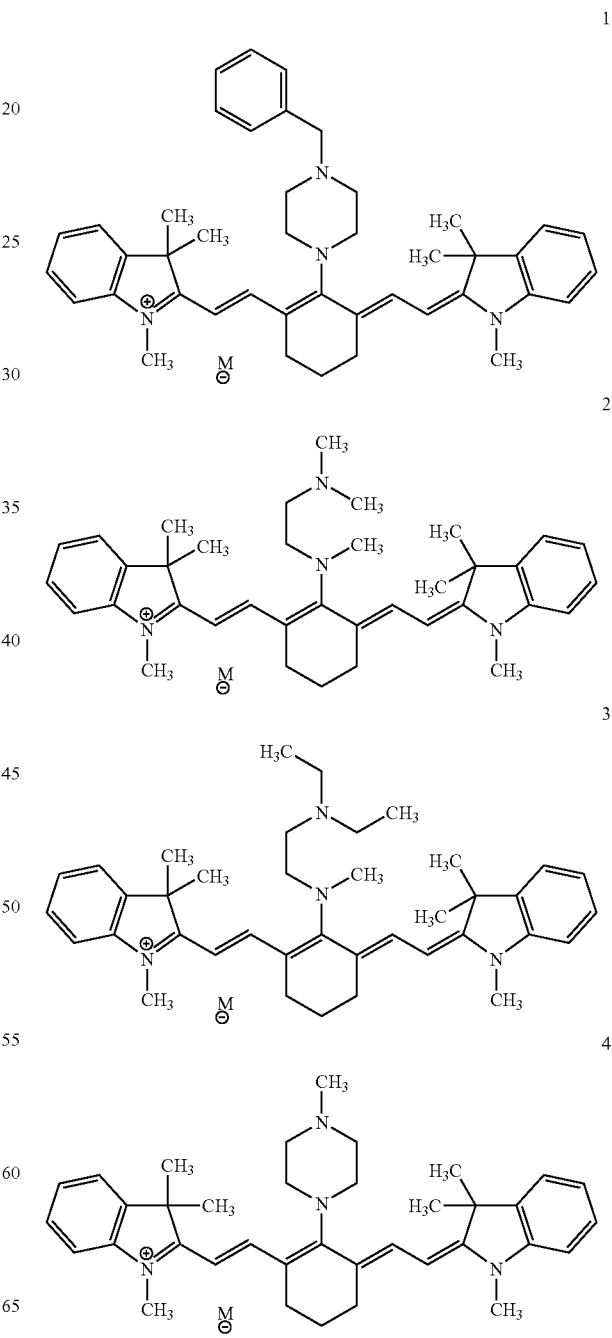

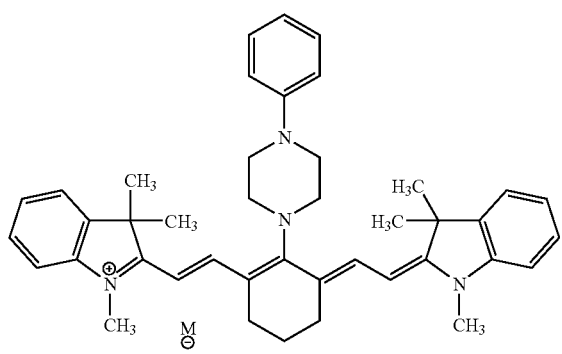

The compounds of the present invention represented by the aforementioned general formula (I) can be prepared by, for example, the method shown in the following scheme. Further, preparation methods of typical compounds included in the aforementioned compounds are specifically shown in Examples of this specification. It can be understood by those skilled in the art that the compounds represented by the aforementioned general formula (I) can be readily prepared by referring to the following scheme and the specific explanations in Examples.

The compounds of the present invention represented by the aforementioned general formula (I), preferably the aforementioned general formula (IA), have properties that (a) they emit strong fluorescence with an excitation light of the near infrared region around 650 to 950 nm, which fluorescence has superior permeability into biological tissues; (b) a nitrogen atom contained in a substituent binding to a methine chain such as $L^1$ but not directly binding to the methine chain is protonated depending on a pH change, and thereby electron donating ability of an atom directly binding to the cyanine fluorophore (preferably nitrogen atom) is decreased; and (c) the compounds show a marked wavelength shift of the peak in the excitation spectrum according to the change of the electron donating ability of the atom directly binding to the cyanine fluorophore (preferably nitrogen atom). This wavelength shift can usually be observed in the range of about 40 to 70 nm depending on pKa of the compounds, and can be observed as a wavelength shift specific to pH without being influenced by metal ions and proteins abundantly existing in the living bodies. Further, by choosing $R^3$, $R^4$ and/or $R^5$ in the general formula (I), preferably $R^{13}$, $R^{14}$, and/or $R^{15}$ in the general formula (IA), from various substituents, a pKa can be arbitrarily adjusted, and thus it is possible to design an optimal compound for detecting a desired pH environment.

[Formula 6]

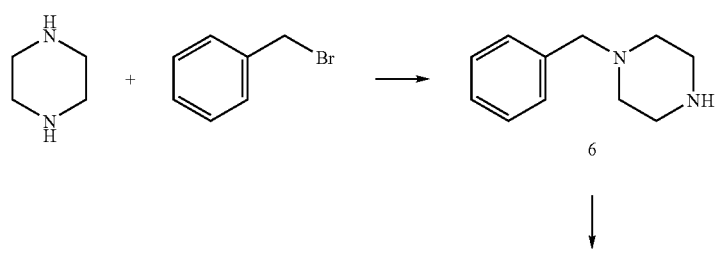

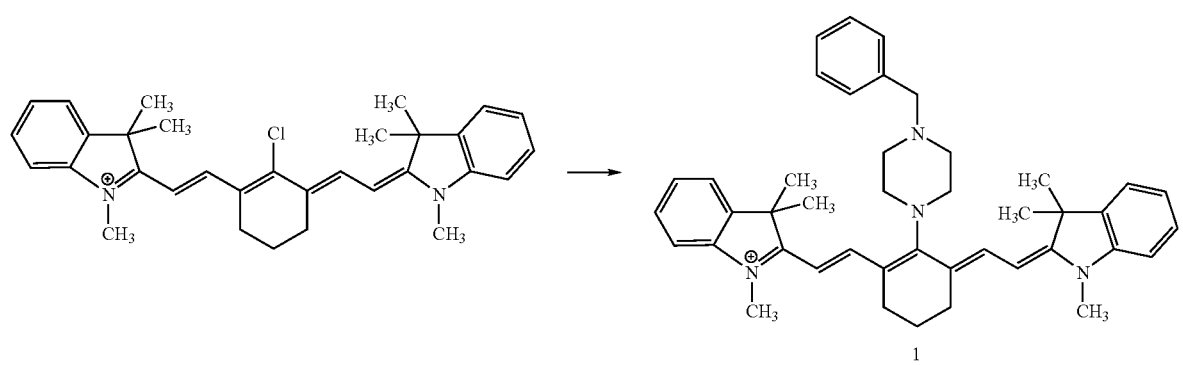

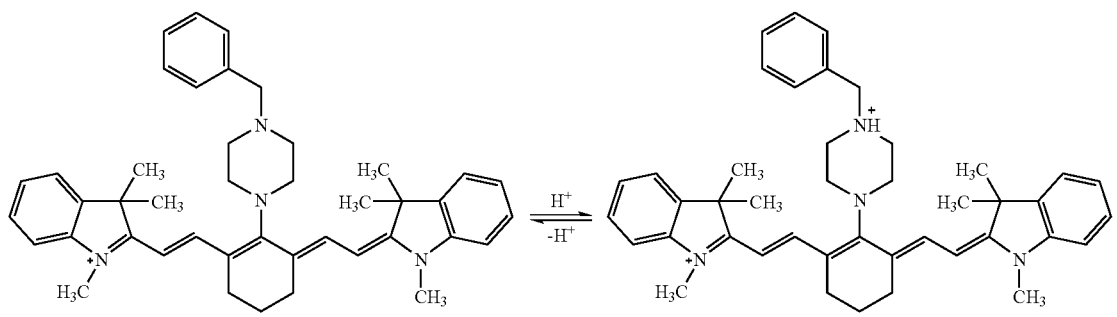

[Formula 7]

By using the compounds of the present invention as a pH fluorescent probe, selecting two appropriately different wavelengths to carry out excitation and measuring a ratio of the fluorescence intensities observed at the time of the excitation, pH can be measured by the ratio method. Therefore, the compounds of the present invention are useful as a pH fluorescent probe for measuring pH especially in live cells, live tissues or the like, in particular deep part tissues, under a physiological condition. The two different wavelengths may be selected in such a manner that fluorescence intensity increases along with the increase of pH at the time of excitation with one wavelength, whilst fluorescence intensity decreases along with the increase of pH at the time of excitation with the other wavelength. The details of the ratio method are described in the book by Mason W. T. (Mason W. T. in Fluorescent and Luminescent Probes for Biological Activity, Second Edition, Edited by Mason W. T., Academic Press), and the like, and specific examples of the measurement method using the compounds of the present invention are also shown in Examples of the specification. The term "measurement" used in the specification should be construed in its broadest sense, including quantitative and qualitative measurements.

The method for using the pH fluorescent probe of the present invention is not particularly limited, and the probe can be used in the same manner as conventionally known pH fluorescent probes. In general, a compound represented by the aforementioned general formula (I) is dissolved in an aqueous medium such as physiological saline or a buffered solution, or in a mixture of an aqueous medium and a water-miscible organic solvent such as ethanol, acetone, ethylene glycol, dimethyl sulfoxide, and dimethylformamide, then the resulting solution is added to a suitable buffered solution containing a test object such as cells or tissues, and the mixture thus obtained is excited with appropriately selected two different wavelengths of the near infrared region around 650 to 950 nm which have superior permeability into biological tissues, and fluorescence intensities can be measured for each excitation.

For example, in the case of Compound 2 mentioned above, the value of the fluorescence intensity at 780 nm obtained with excitation at 750 nm relative to the fluorescence intensity at 780 nm obtained with excitation at 670 nm in an aqueous solution of pH 4 is slightly smaller than 2. The value of the fluorescence intensity at 780 nm obtained with excitation at 750 nm relative to the fluorescence intensity at 780 nm obtained with excitation at 670 nm decreases along with the increase of pH, and it becomes about 0.6 at pH 10. Thus, by measuring the fluorescence intensity ratio at 780 nm obtained with excitation at 670 nm and 750 nm, pH can be calculated.

The pH fluorescent probe of the present invention may be combined with an appropriate additive and used in the form of a composition. For example, it may optionally be combined with additives such as buffers, and dissolving aids.

EXAMPLES

The present invention will be more specifically explained with reference to examples. However, the scope of the present invention is not limited to the following examples. The compound numbers used in the following examples correspond to those of the preferred compounds mentioned above.

Example 1

Synthesis of Compound 1

(A) Synthesis of Compound 6

Anhydrous piperazine (2.2 g, 26 mmol) was dissolved in dichloromethane (20 mL). Under ice cooling, this solution was added drop wise with a solution of benzyl bromide (3.4 g, 13 mmol) in dichloromethane (20 mL). After completion of the addition, the mixture was stirred at room temperature for 6 hours. The solvent was evaporated under reduced pressure, and the residue was subjected to silica gel column chromatography to obtain Compound 6 (850 mg).

(B) Synthesis of Compound 1

IR786 (CAS NO. 115970-66-6, 60 mg, 0.1 mmol) was dissolved in dehydrated dimethylformamide (5 mL). Compound 6 (70 mg, 0.4 mmol) was added to this solution, and the mixture was stirred at room temperature for 5 hours under an argon atmosphere. The solvent was evaporated under reduced pressure, and then the residue was subjected to column chromatography using NH silica gel. The obtained compound was washed with hexane to obtain Compound 1 (62 mg).

$^1$H-NMR (300 MHz, CDCl$_3$) δ 1.62 (s, 12H), 1.78-1.87 (m, 2H), 2.42 (br, 4H), 2.48 (t, 4H, J=6.42 Hz), 3.49 (s, 6H), 3.74 (s, 2H), 3.78 (br, 4H), 5.76 (d, 2H, J=13.4 Hz), 7.00 (d, 2H, J=7.86 Hz), 7.12 (t, 2H, J=7.53 Hz), 7.28-7.40 (m, 7H), 7.59 (d, 2H, J=13.4 Hz)

$^{13}$C-NMR (75 MHz, CDCl$_3$) δ 21.6, 24.9, 28.8, 30.8, 47.8, 54.1, 55.0, 62.9, 96.0, 109.1, 121.8, 123.4, 124.4, 127.5, 128.4, 128.5, 129.4, 136.6, 139.9, 141.1, 143.2, 169.1, 173.7

HRMS (ESI+) calcd 623.4139, found 623.4113 (M+)

Example 2

Syntheses of Compounds 2 to 5

Compounds 2 to 5 were synthesized in the same manner as that of Example 1 mentioned above.

Compound 2

¹H-NMR (300 MHz, CD₃OD) δ 1.54 (s, 12H), 1.69-1.78 (m, 2H), 2.12 (s, 6H), 2.42 (t, 4H, J=6.60 Hz), 2.64 (t, 2H, J=6.10 Hz), 3.35 (s, 3H), 3.37 (s, 6H), 3.80 (t, 2H, J=6.10 Hz), 5.77 (d, 2H, J=13.4 Hz), 6.98-7.03 (m, 4H), 7.19-7.31 (m, 4H), 7.62 (d, 2H, J=13.4 Hz)

¹³C-NMR (75 MHz, CDCl₃) δ 21.8, 24.1, 28.6, 28.9, 30.5, 44.4, 45.0, 47.7, 57.3, 95.1, 108.8, 121.8, 123.0, 123.2, 128.2, 139.9, 142.1, 143.3, 169.0, 176.1

HRMS (ESI+) calcd 549.3957, found 549.3967 (M+)

Compound 3

¹H-NMR (300 MHz, CDCl₃) δ 1.04 (t, 6H, J=7.06 Hz), 1.67 (s, 12H), 1.83-1.87 (m, 2H), 2.48 (t, 4H, J=6.24 Hz), 2.58 (q, 4H, J=7.06 Hz), 2.89 (br, 2H), 3.48 (s, 6H), 3.53 (s, 3H), 3.91 (t, 2H, J=6.10 Hz), 5.73 (d, 2H, J=13.4 Hz), 6.98 (d, 2H, J=7.89 Hz), 7.10 (t, 2H, J=7.43 Hz), 7.29-7.34 (m, 4H), 7.58 (d, 2H, J=13.4 Hz)

¹³C-NMR (75 MHz, CDCl₃) δ 10.9, 21.7, 24.2, 29.1, 30.5, 44.8, 46.6, 47.7, 50.9, 55.2, 95.2, 108.8, 121.8, 123.0, 128.3, 139.9, 141.7, 143.3, 168.8, 175.8

HRMS (ESI+) calcd 577.4270, found 577.4278 (M+)

Compound 4

¹H-NMR (300 MHz, CD₃OD) δ 1.59 (s, 12H), 1.72-1.76 (m, 2H), 2.38 (s, 3H), 2.44 (t, 4H, J=6.42 Hz), 2.66 (br, 4H), 3.42 (s, 6H), 3.67 (t, 4H, J=4.77 Hz), 5.85 (d, 2H, J=13.4 Hz), 7.04-7.08 (m, 4H), 7.23-7.35 (m, 4H), 7.69 (d, 2H, J=13.4 Hz)

¹³C-NMR (75 MHz, CDCl₃) δ 21.6, 24.9, 28.8, 30.8, 46.1, 47.9, 54.9, 56.5, 96.2, 109.2, 121.8, 123.4, 124.4, 128.4, 139.9, 141.2, 143.2, 169.3, 173.6

HRMS (ESI+) calcd 547.3800, found 547.3815 (M+)

Compound 5

¹H-NMR (300 MHz, CDCl₃) δ 1.62 (s, 12H), 1.82-1.90 (m, 2H), 2.53 (t, 4H, J=6.51 Hz), 3.47 (t, 4H, J=4.60 Hz), 3.53 (s, 6H), 3.89 (t, 4H), 5.76 (d, 2H, J=13.4 Hz), 6.96-7.39 (m, 13H), 7.73 (d, 2H, J=13.4 Hz)

¹³C-NMR (75 MHz, CDCl₃) δ 21.6, 25.0, 28.7, 30.9, 48.0, 51.2, 54.7, 96.8, 109.3, 116.6, 120.8, 121.8, 123.6, 125.1, 128.4, 140.0, 141.4, 143.2, 150.6, 169.7, 172.7

HRMS (ESI+) calcd 609.3994, found 609.3957 (M+)

Example 3

Optical Characteristics of Compounds 1 to 5 in Various pH Environments

Figure 2:
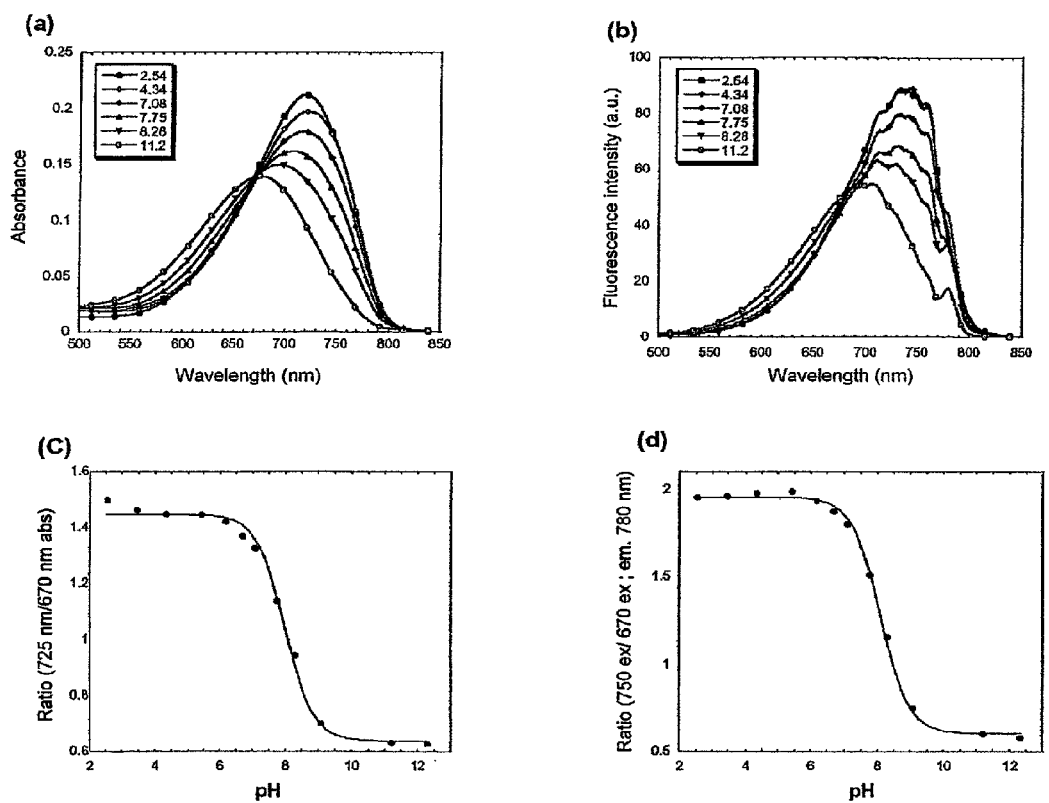
FIG. 2 shows the optical characteristics of Compound 2 at various pH values. In the drawings, (a) shows the absorption spectrum, (b) shows the excitation spectrum at a fluorescence wavelength of 780 nm, (c) shows ratio of absorption at 725 nm to absorption at 670 nm, and (d) shows ratio of fluorescence intensity at 780 nm observed with excitation at 750 nm to fluorescence intensity at 780 nm observed with excitation at 670 nm. All the measurements were performed in a 100 mM sodium phosphate buffered solution containing 0.1% DMSO as an auxiliary solvent.
Figure 3:
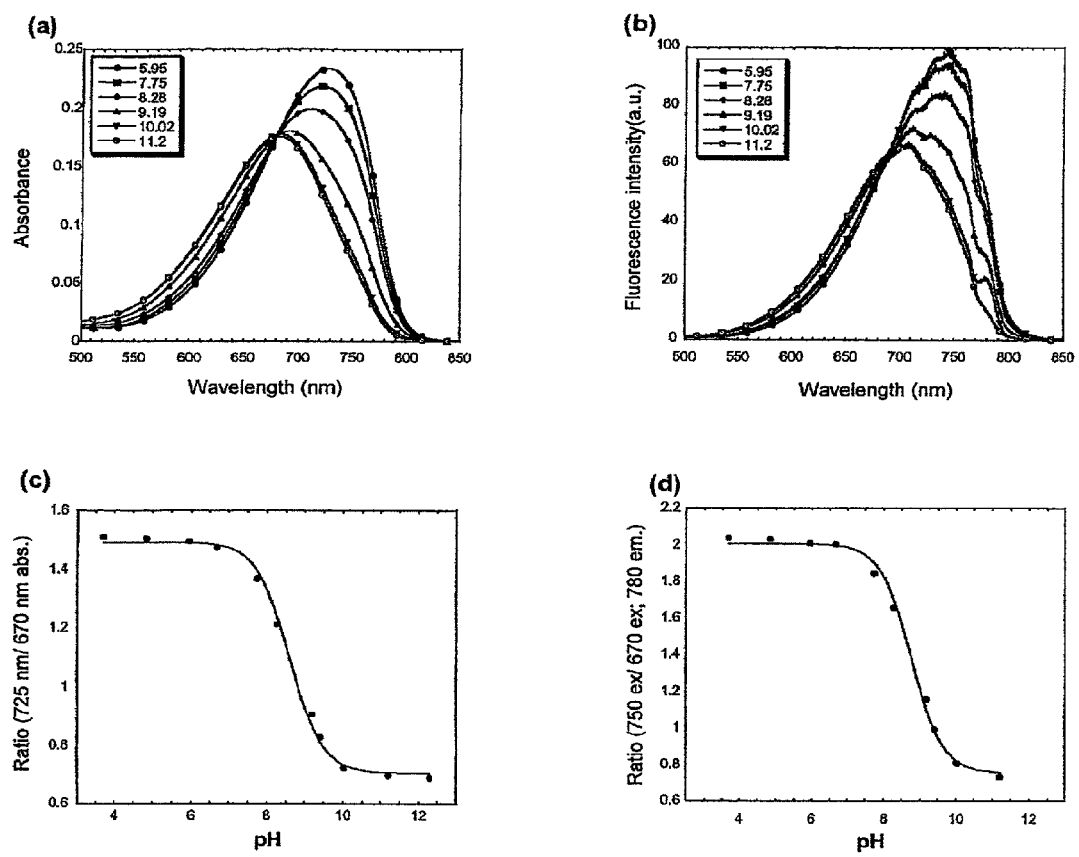
FIG. 3 shows the optical characteristics of Compound 3 at various pH values. In the drawings, (a) shows the absorption spectrum, (b) shows the excitation spectrum at a fluorescence wavelength of 780 nm, (c) shows ratio of absorption at 725 nm to absorption at 670 nm, and (d) shows ratio of fluorescence intensity at 780 nm observed with excitation at 750 nm to fluorescence intensity at 780 nm observed with excitation at 670 nm. All the measurements were performed in a 100 mM sodium phosphate buffered solution containing 0.1% DMSO as an auxiliary solvent.
Figure 4:
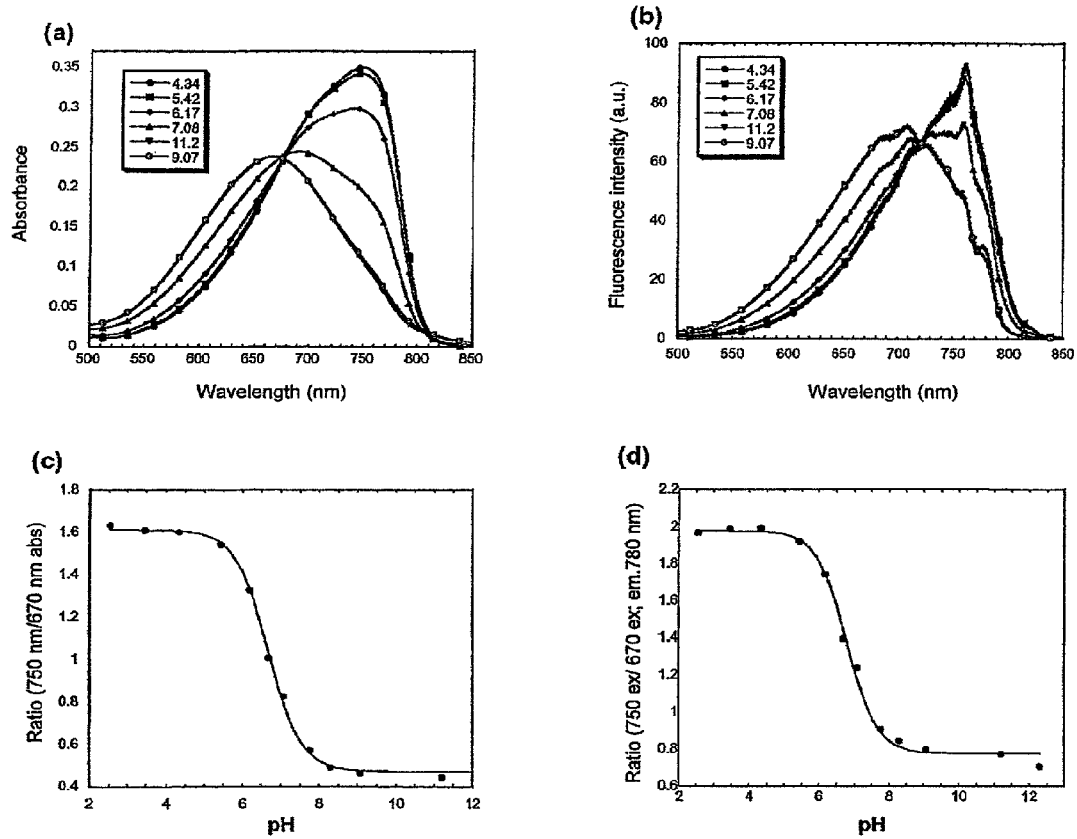
FIG. 4 shows the optical characteristics of Compound 4 at various pH values. In the drawings, (a) shows the absorption spectrum, (b) shows the excitation spectrum at a fluorescence wavelength of 780 nm, (c) shows ratio of absorption at 750 nm to absorption at 670 nm, and (d) shows ratio of fluorescence intensity at 780 nm observed with excitation at 750 nm to fluorescence intensity at 780 nm observed with excitation at 670 nm. All the measurements were performed in a 100 mM sodium phosphate buffered solution containing 10% DMSO as an auxiliary solvent.
Figure 5:
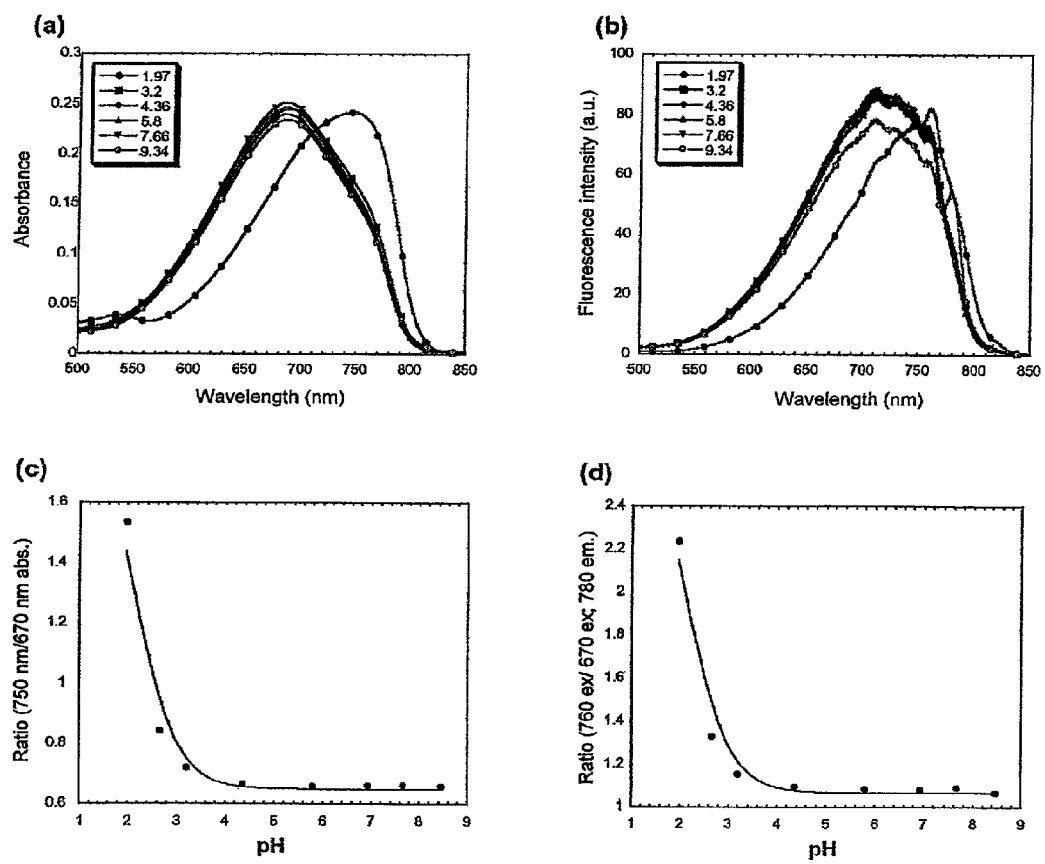
FIG. 5 shows the optical characteristics of Compound 5 at various pH values. In the drawings, (a) shows the absorption spectrum, (b) shows the excitation spectrum at a fluorescence wavelength of 780 nm, (c) shows ratio of absorption at 750 nm to absorption at 670 nm, and (d) shows ratio of fluorescence intensity at 780 nm observed with excitation at 760 nm to fluorescence intensity at 780 nm observed with excitation at 670 nm. All the measurements were performed in a 100 mM sodium phosphate buffered solution containing 10% DMSO as an auxiliary solvent.

Results of measurement of absorption spectra and excitation spectra of Compounds 1 to 5 in phosphate buffered solution of various pH values as well as ratios of absorbance at 750 nm or 725 nm to absorbance at 670 nm observed in the measurement and ratios of fluorescence intensity at 780 nm obtained by excitation with an excitation light of 750 nm or 760 nm to fluorescence intensity at 780 nm obtained by excitation with an excitation light of 670 nm observed in the measurement are shown in FIGS. 1 to 5. It can be seen that the maximum peaks in the absorption spectra and excitation spectra shifted to the longer wavelength side along with the decrease of pH for all the compounds. Further, from the ratios of absorbance at 750 nm or 725 nm to absorbance at 670 nm and the ratios of fluorescence intensity at 780 nm obtained by excitation with an excitation light of 750 nm or 760 nm to fluorescence intensity at 780 nm obtained by excitation with an excitation light of 670 nm measured in phosphate buffered solution of various pH values, it can be seen that the ratios of absorbance values of the compounds at two different wavelengths and the ratios of fluorescence intensities of the compounds obtained by excitation with lights of different two wavelengths changed in a pH-dependent manner, and thus all the compounds are useful as a pH probe.

Example 4

Control of pKa of Compounds by Changing Structure

The pKa values of Compounds 1 to 5 are as shown in Table 1. By using the pH probe described in the present invention, change of pH can be detected in a range including pKa of the compound according to the fluorescence ratio method or the absorbance ratio method. Compounds 1 to 5 have different pKa values, and accordingly, pH ranges suitable for the detection are different among them. Therefore, a pH probe suitable for a pH range desired to be detected can be chosen and used by utilizing the difference. Similarly, by suitably choosing $R^3$, $R^4$ and/or $R^5$ in the general formula (I), or $R^{13}$, $R^{14}$ and/or $R^{15}$ in the general formula (IA), a pH probe having a desired pKa and thus suitable for measurement of a desired pH range can be designed and provided.

TABLE 1

| | pH probe | | | | |
|---|---|---|---|---|---|
| | 1 | 2 | 3 | 4 | 5 |
| pKa | 5.5 | 8.1 | 8.7 | 6.8 | 2.1 |

What is claimed is:

1. A compound having one of the following structures:

-continued

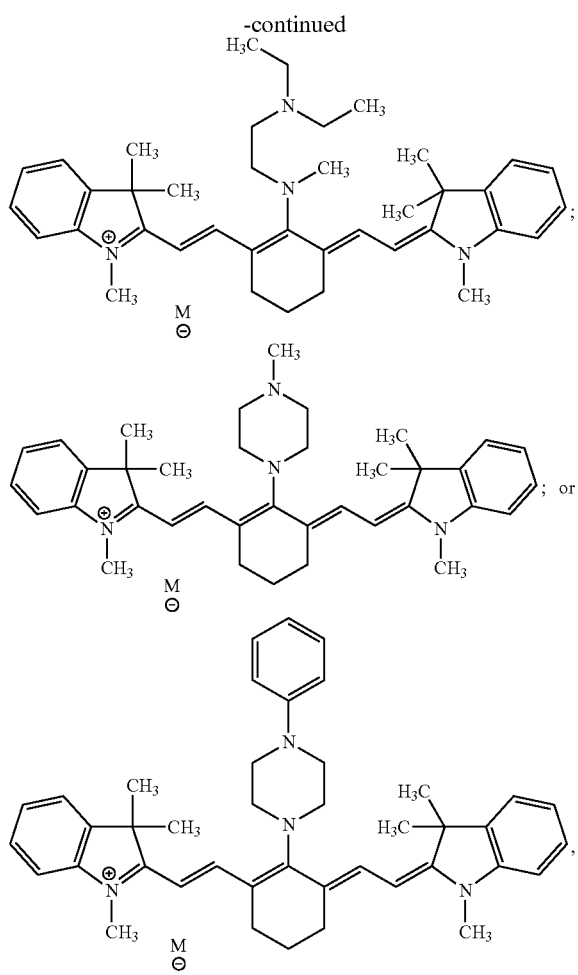

wherein M⁻ represents a counterion in a number required for neutralizing electrical charge.

2. A compound according to claim 1 having the following structure:

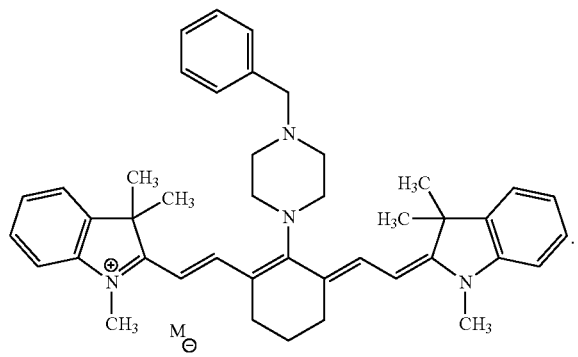

3. A pH fluorescent probe containing the compound according to claim 2.

4. A method for measuring pH of a test object, which comprises:
(a) contacting the compound of claim 2 with the test object, and
(b) measuring fluorescence intensity of the resulting compound after the contacting in (a).

5. The method according to claim 4, wherein the measuring fluorescence intensity of (b) includes excitation with two different wavelengths and measuring a ratio of fluorescent intensities.

6. The method according to claim 5, wherein the test object is a cell or a tissue.

7. A compound according to claim 1 having the following structure:

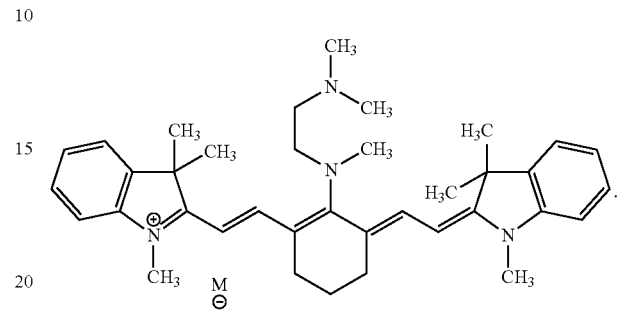

8. A pH fluorescent probe containing the compound according to claim 7.

9. A method for measuring pH of a test object, which comprises:
(a) contacting the compound of claim 7 with the test object, and
(b) measuring fluorescence intensity of the resulting compound after the contacting in (a).

10. The method according to claim 9, wherein the measuring fluorescence intensity of (b) includes excitation with two different wavelengths and measuring a ratio of fluorescent intensities.

11. The method according to claim 10, wherein the test object is a cell or a tissue.

12. A compound according to claim 1 having the following structure:

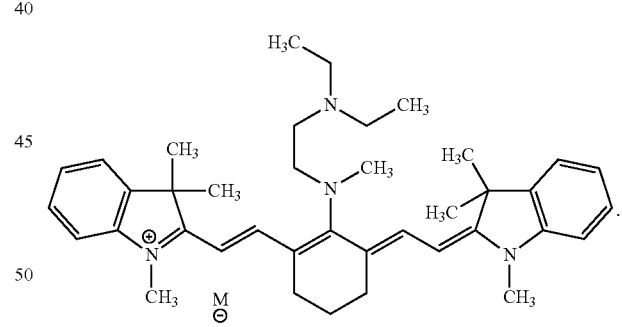

13. A pH fluorescent probe containing the compound according to claim 12.

14. A method for measuring pH of a test object, which comprises:
(a) contacting the compound according to claim 12 with the test object, and
(b) measuring fluorescence intensity of the resulting compound after the contacting in (a).

15. The method according to claim 14, wherein the measuring fluorescence intensity of (b) includes excitation with two different wavelengths and measuring a ratio of fluorescent intensities.

16. The method according to claim 14, wherein the test object is a cell or a tissue.

17. A compound according to claim 1 having the following structure:

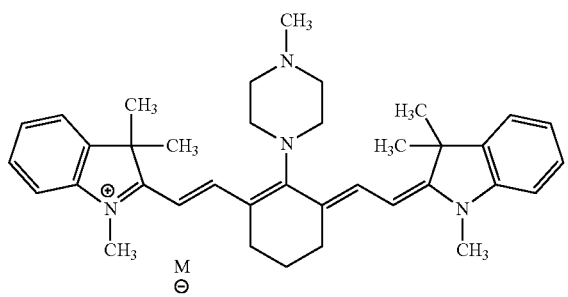

18. A pH fluorescent probe containing the compound according to claim 17.

19. A method for measuring pH of a test object, which comprises:
   (a) contacting the compound according to claim 17 with the test object, and
   (b) measuring fluorescence intensity of the resulting compound after the contacting in (a).

20. The method according to claim 19, wherein the test object is a cell or a tissue.

21. The method according to claim 19, wherein the measuring fluorescence intensity of (b) includes excitation with two different wavelengths and measuring a ratio of fluorescent intensities.

22. The method according to claim 21, wherein the test object is a cell or a tissue.

23. A compound according to claim 1 having the following structure:

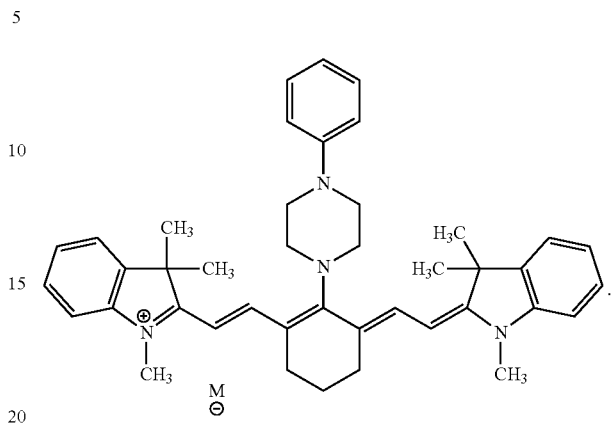

24. A pH fluorescent probe containing the compound according to claim 23.

25. A method for measuring pH of a test object, which comprises:
   (a) contacting the compound of claim 23 with the test object, and
   (b) measuring fluorescence intensity of the resulting compound after the contacting in (a).

* * * * *